United States Patent
Gogol, Jr.

(10) Patent No.: US 9,182,378 B2
(45) Date of Patent: Nov. 10, 2015

(54) HIGH CAPACITY MONITOR CRYSTAL EXCHANGER UTILIZING AN ORGANIZED 3-D STORAGE STRUCTURE

(71) Applicant: Inficon, Inc., East Syracuse, NY (US)

(72) Inventor: Carl A. Gogol, Jr., Manlius, NY (US)

(73) Assignee: Inficon, Inc., East Syracuse, NY (US)

( * ) Notice: Subject to any disclaimer, the term of this patent is extended or adjusted under 35 U.S.C. 154(b) by 424 days.

(21) Appl. No.: 13/841,014

(22) Filed: Mar. 15, 2013

(65) Prior Publication Data

US 2014/0260621 A1    Sep. 18, 2014

(51) Int. Cl.
| | |
|---|---|
| G01N 29/04 | (2006.01) |
| B05C 11/00 | (2006.01) |
| G01N 29/12 | (2006.01) |
| G01N 29/24 | (2006.01) |

(52) U.S. Cl.
CPC ............ *G01N 29/12* (2013.01); *G01N 29/2443* (2013.01); *G01N 2291/106* (2013.01)

(58) Field of Classification Search
CPC ................................ G01N 29/04; B05C 11/00
USPC ............................................. 73/579; 374/117
See application file for complete search history.

(56) References Cited

U.S. PATENT DOCUMENTS

| | | | | |
|---|---|---|---|---|
| 3,383,238 | A * | 5/1968 | Unzicker et al. ................ 427/10 |
| 3,504,376 | A * | 3/1970 | Reid et al. ..................... 436/165 |
| 3,545,935 | A * | 12/1970 | Kearns .......................... 422/417 |
| 4,362,125 | A | 12/1982 | Schadler |
| 5,025,664 | A | 6/1991 | Kendrick et al. |
| 5,117,192 | A * | 5/1992 | Hurd ............................. 324/727 |
| 5,948,983 | A * | 9/1999 | Gogol et al. .................... 73/579 |
| 6,668,618 | B2 * | 12/2003 | Larson et al. ................ 73/24.01 |
| 6,989,133 | B1 * | 1/2006 | Heimberg et al. ............ 422/131 |
| 2002/0152803 | A1 * | 10/2002 | Larson et al. ................ 73/64.53 |

* cited by examiner

*Primary Examiner* — Lisa Caputo
*Assistant Examiner* — Jamel Williams
(74) *Attorney, Agent, or Firm* — Barclay Damon, LLP (57) ABSTRACT

An apparatus for monitoring and detecting material deposited onto a substrate during a deposition process in a processing chamber includes a storage structure having a primary axis extending between respective first and second ends and an exterior lateral surface between the first and second ends extending about the primary axis. A plurality of monitor crystals are supported by the storage structure at spaced positions along said exterior lateral surface and in which a drive mechanism advances the storage structure rotatably and axially relative to the primary axis such that at least one monitor crystal is advanced or retracted relative to at least one measuring position. A retained crystal that is advanced to the measuring position can be electrically connected, using a brush contact or other mechanism, in order to excite the crystal using a resonance circuit.

39 Claims, 9 Drawing Sheets

HIGH CAPACITY MONITOR CRYSTAL EXCHANGER UTILIZING AN ORGANIZED 3-D STORAGE STRUCTURE

TECHNICAL FIELD

The application relates generally to the field of monitoring and controlling the deposit of materials on substrates, such as by vapor or chemical deposition. More specifically, this application relates to high capacity quartz crystal deposition sensors, in which the resonance frequency of a piezoelectric crystal is monitored, and in which changes in resonance frequency correspond to changes in thickness of deposited material. Even more specifically, this application relates to a structure enabling high capacity retention of multiple monitor crystals in a three-dimensional framework that can be moved relative to a processing chamber, allowing one of more monitor crystals to be indexed in turn to permit monitoring and control functions to be maintained.

BACKGROUND

Quartz crystal sensors have been widely used to monitor vacuum deposition processes and to accurately control the amount of material that is deposited as well as the rate of deposit onto a surface, such as a substrate used for semiconductor, optics or display processing. In these sensors, one more piezoelectric crystals which can be manufactured from quartz, barium titanate, or another suitable material, are connected into a resonance circuit so that that the natural resonant frequency of one crystal can be monitored, the crystal being positioned in relation to the interior of the processing chamber. The natural resonance is primarily dependent upon total mass and geometry of the crystal, wherein the resonance frequency drops in relation to the amount of material that is coated onto the crystal during a vacuum deposition process. However, as the deposited material builds up, the sharpness of the composite resonance diminishes, and eventually a point is reached in which the crystal cannot adequately monitor the process accurately or effectively. At this point, the piezoelectric crystal must be replaced.

A number of multi-crystal sensor heads have been developed, including those described by U.S. Pat. No. 5,025,664, for use in multi-crystal quartz oscillator deposition monitors and in which a plurality of crystals can be rotated about a rotary carousel. Other versions have been developed, such as described, for example, in U.S. Pat. Nos. 4,362,125 and 3,383,238. Each of the foregoing designs, however, are typified by a two-dimensional structure that outwardly increases the overall size of the sensor head as the number of crystals increases.

According to one aspect, there is provided a high capacity piezoelectric crystal deposition sensor for use in detecting and monitoring changes in a deposited material in a processing chamber, said sensor comprising:

a three dimensional storage structure having a primary axis extending between respective first and second ends and an exterior lateral surface between said first and second ends extending about said primary axis;

a plurality of piezoelectric crystals supported by said storage structure at spaced positions along said exterior lateral surface; and a drive mechanism for rotating and axially advancing or retreating said storage structure relative to the primary axis such that at least one piezoelectric crystal can be advanced relative to at least measuring position and a mechanism for electrically exciting the at least one advanced crystal and enable detection due to accumulating material on said crystal.

According to another aspect, there is provided a three-dimensional storage structure for use in a crystal deposition sensor, said three-dimensional storage structure comprising:

a carrier body having a primary axis extending between a first end and a second opposite end, the carrier body further having a lateral exterior surface defined between the first and second ends and extending about the primary axis; and a plurality of retaining cavities disposed at spaced axial positions along the lateral exterior surface of the carrier body, each retaining cavity being sized for retaining a piezoelectric monitor crystal.

According to yet another version, there is provided a method of exchanging crystals used in a crystal deposition monitor, said method comprising the steps of:

disposing a plurality of piezoelectric crystals in spaced relation onto the exterior surface of a three-dimensional storage structure;

axially and rotatably advancing or retreating the storage structure in order to index at least one piezoelectric crystal relative to at least one measuring position;

electrically exciting the advanced piezoelectric crystal;

detecting the change of mass of material applied to a substrate;

axially and rotatably advancing or retreating the storage structure along a primary axis of the three-dimensional storage structure in order to index at least one other monitor crystal into the at least one sensor aperture.

The herein described storage structure can be used for the process control of the growth rate and associate thickness determination for an applicable process of specific materials onto a substrate in which the material is transported by one of several means from a material source to the substrate. The transport may be through media that may be essentially a vacuum or any rarified or pressurized media, as required by the process.

Examples of the foregoing can include vacuum evaporation that involves material transport from a hot source of material through a vacuum to the substrate. There are also many various means of sputtering in which ionized atoms of a gas intervening between the source and the substrate are used to energetically impinge upon a target material and the resulting eroded material fragments pass through the gas mixture to the substrate and substantially adhere to the substrate. Other less common means of material transport include laser induced ablation of the target, plasma ionization and arc deposition. All of these methods commonly include a step of transport of the material from a source (or target) through a vacuum or other process media and finally impingement and collection onto a substrate or onto a monitor crystal being used as a surrogate substrate.

A high capacity crystal exchange mechanism is therefore described that utilizes a moving three-dimensional monitor crystal storage element or storage structure. All stored monitor crystals have individual fixed locations and are arrayed on a complexly shaped surface, such as a cylinder or other polygon, in a predetermined arrangement. The particular array of monitor crystal locations chosen should be designed to facilitate the efficient movement of monitor crystals relative to at least one measuring position. In a preferred version, the three-dimensional storage structure is a cylindrical body having the monitor crystals retained in helical sequential form on a curved surface. Individual monitor crystals may be positioned at least one at a time into a position useful for receiving the flow of a deposition material, in which the crystals can be retained directly or within individual monitor crystal packages that facilitate the loading and unloading of the storage structure. In one version, motion of a point on the surface of the storage structure during sequential movement of monitor crystals into the working position is helical in nature and in which movement of the three-dimensional storage structure induces a change in the monitor crystal. This movement may be arbitrary in nature with sufficiently complex motion, inducing mechanisms that include one or more stepper motors or other suitable actuators, wherein the drive mechanism causes both rotational and axial movement about the primary axis of the storage structure.

One advantage provided by the herein described apparatus is that a high quantity monitor crystal storage capacity can be achieved in a low volume package, and in which greater numbers of crystals can be retained as opposed to conventionally known sensor heads utilizing two-dimensional crystal storage.

Another advantage is the ability to test cycle the storage structure in order to verify acceptable electrical operation of all piezoelectric crystals prior to closing the vacuum system and their subsequent use during deposition.

Yet another advantage is that the herein described apparatus enables a modular design approach that facilitates and eases the development of different capacity versions to meet the quantities of piezoelectric crystals required for a wide variety of processes that have adequate reserve capacity to meet desired maintenance intervals.

According to one version, a core mechanism can be provided for making electrical contact to the crystals and executing the organized flow of piezoelectric crystals into the measurement position. This core measurement and transport component will easily interface with various drive mechanisms for powering the crystal exchange process. Attachable drive mechanisms can include both in vacuum and non-vacuum drive power sources.

The system design can include a fluid based mechanism for extracting (or adding) heat to the overall exchanger mechanism in order to stabilize the retained crystal's temperature. The foregoing mechanism will extract the absorbed heat of radiation, the heat of condensation from the deposition sources, losses from drive motors or other ancillary sources of process heating.

The monitor crystals can also be retained for measuring other system parameters, such as temperature.

Advantageously, an apparatus including the present design is not dependent on any particular monitor crystal's size or shape. As such, crystals having a smaller area can be provided to the extent the crystal's vibration is confined to a central area and isolated from contact points (i.e., edges) and wherein the crystal face is not planar; for example, about a spherical surface.

Because smaller crystals can be used, a lower volume exchanger can be provided for the same number of monitor crystals.

In addition, another advantageous feature is the ability to easily replace monitor crystals within the defined structure.

These and other features and advantages will be readily apparent from the following Detailed Description, which should be read in conjunction with the accompanying drawings.

DETAILED DESCRIPTION

The following description relates to a three (3) dimensional crystal head storage structure for use in a crystal deposition monitor and related method for utilizing the storage structure in which a greater plurality of monitor crystals can be retained, indexed, reindexed and replaced, as needed. Throughout the description that follows, certain terms such as "top", "bottom", "upper", "lower", "lateral", "distal" and "proximal" are frequently used to provide a suitable frame of reference with regard to the accompanying drawings. These terms, however, should not be interpreted narrowly in terms of the invention and in accordance with the claims.

The drawings used are intended to provide sufficient details as to the workings and design of the exemplary embodiment. However, the drawings are not necessarily drawn to a particular scale.

As used herein, the terms "a", "an" and "the" are articles that can equally refer to one or more than one.

As used herein, the terms "comprise", "comprises", and "comprising" relate to open-ended transitional terms.

As used herein, the terms "includes", "contains" and "including", unless specifically indicated otherwise, are intended to be synonymous with the open-ended transitional terms "comprise", "comprises" and "comprising", noted above.

Figure 1:
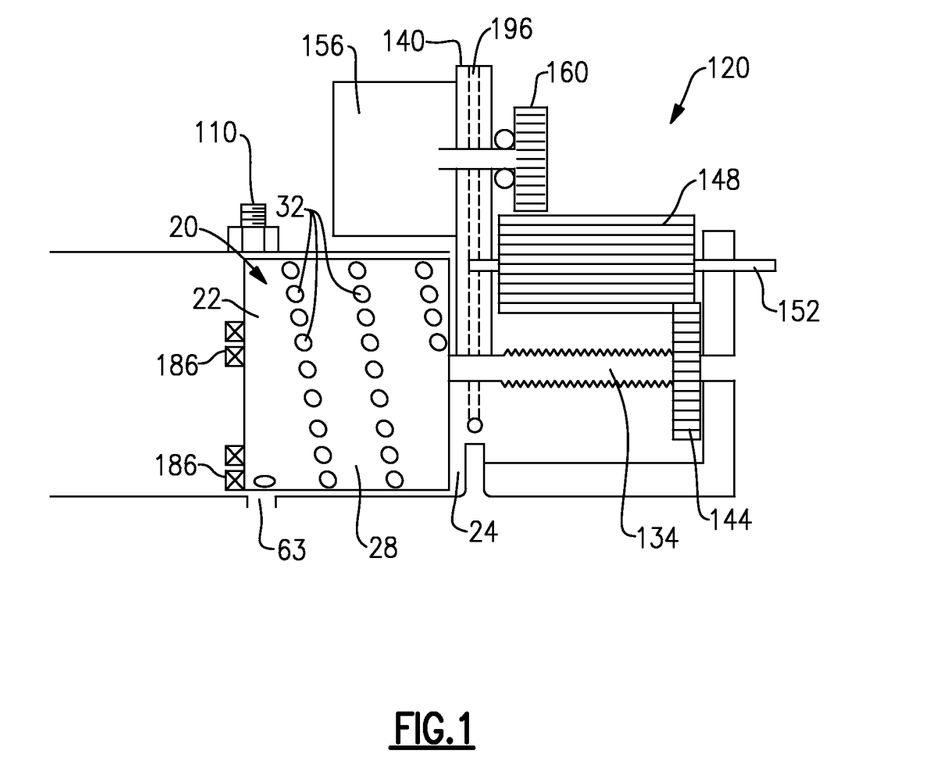
FIG. 1 is a perspective view of a three-dimensional storage structure made in accordance with a first embodiment including an exemplary drive mechanism and temperature controlling mechanism.

A three (3) dimensional storage structure 20 is shown in FIG. 1 comprising a first end 22, a second end 24 and an exterior lateral surface 28 that is defined between the first and second ends 22, 24 of the structure 20. According to this embodiment, the storage structure 20 is substantially cylindrical in configuration and is defined by a curved lateral exterior surface 28. However, the storage structure 20 can alternatively assume other polygonal shapes (e.g., pentagonal, hexagonal, etc.). The storage structure 20 is provided with a plurality of retaining cavities 32 that are equally spaced about the exterior lateral surface 28. As further discussed herein, the retaining cavities 32 are preferably disposed along a substantially helical path between the first and second ends 22, 24 of the structure 20 wherein each retaining cavity 32 is sized and configured for receiving a crystal monitor package 40, FIG. 2, as discussed herein. The storage structure 20 is hollow, such that each retaining cavity 32, FIG. 2, extends substantially through the thickness of the exterior lateral surface 28 with a smaller aligned opening 33 extending into the hollow interior of the storage structure 20, thereby creating exterior and interior openings, respectively.

Figure 2:
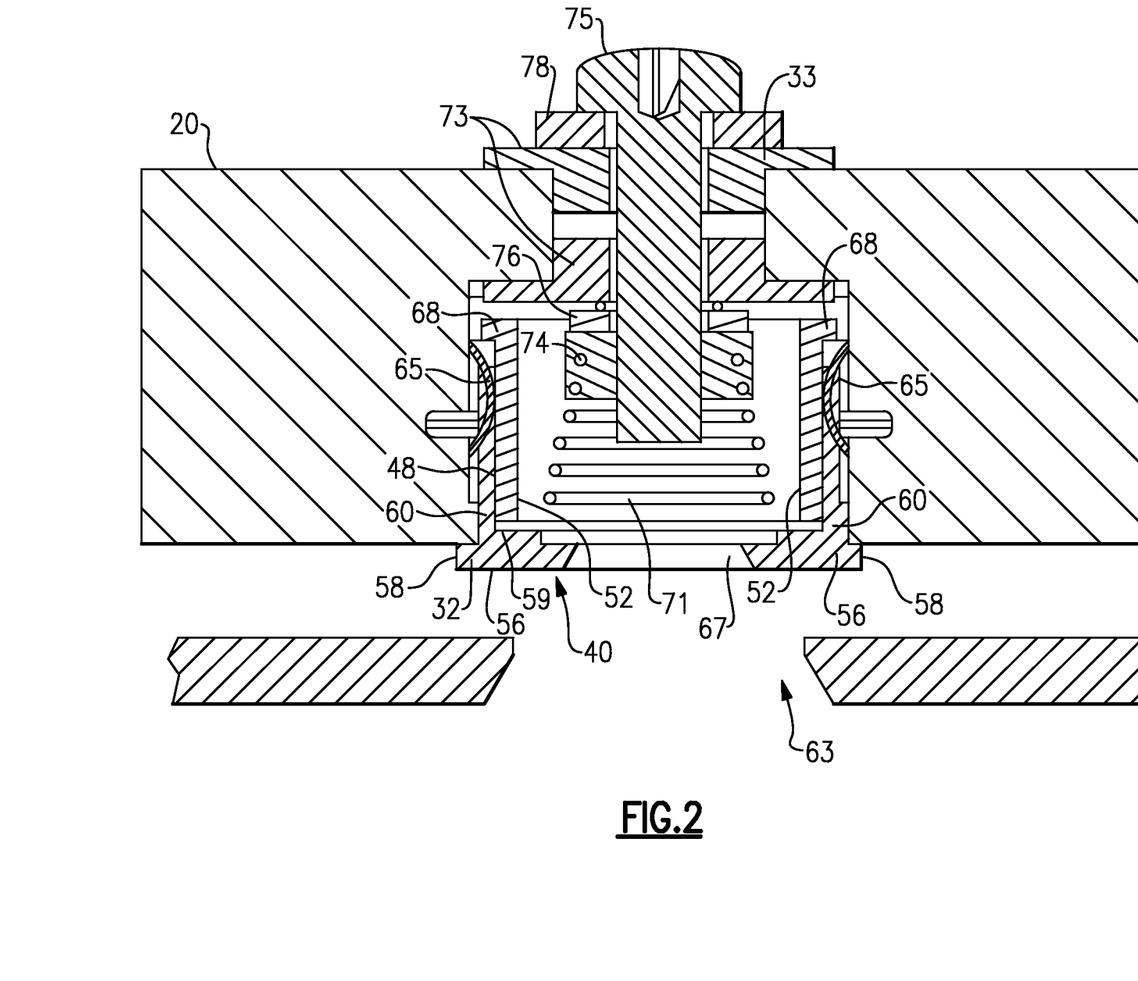
FIG. 2 is a sectioned view of a crystal holder assembly in accordance with an exemplary embodiment for use within the three dimensional storage structure of FIG. 1.

Referring to FIG. 2, a crystal monitor package 40 in accordance with an exemplary embodiment includes a monitor crystal 44, a holder assembly 48, and an insulating retainer 52 that is placed within the holder assembly 48. According to this embodiment, the holder assembly 48 is preferably made from a metal, such as stainless steel or other suitable electrically conductive material and is defined by a cylindrically shaped member having a planar bottom support portion 56, forming a platform for a monitor crystal 44, as well as vertically disposed side walls 60.

The monitor crystals 44 used and individually retained by the holder assemblies 48 are piezoelectric crystals, such as described in U.S. Pat. No. 5,117,192 to Hurd, the entire contents of which are herein incorporated by reference. In brief, each monitor crystal 44 is configured to resonate when electrically excited and in which the resonant frequency of the crystal 44 drops as material is deposited onto the crystal 44, acting as a surrogate substrate that is directly exposed to a processing chamber via a material aperture 63. According to the exemplary embodiment and as shown in FIG. 2(*b*), a small peripheral notch 59 is formed between the support portion 56 and the cylindrical side wall 60 of the holder assembly 48. This notch 59 insures the monitor crystal 44 can lay flat on the support portion 56 without undue care undertaken to make the inside corner square so as not to suspend the monitor crystal 44 above the support portion 56. The support portion 56 includes an extending annular flange 58 that engages the lateral exterior surface 28 of the storage structure 20 and acts as a mechanical stop for an assembled holder package 40.

The retained insulating retainer 52 can assume various designs, but the essential features of this component are: a) to insure that the monitor crystal 44 is not allowed to fall out of the holder assembly 48 during the process of installation of the monitor package 40 into the organized storage structure 20; and b) to provide sufficient open area to allow a contact mechanism, such as a contact spring 71 configured to pass through the interior of the hollow storage structure 20 and make electrical contact with the monitor crystal 44. According to the exemplary embodiment, the retaining insulator 52 is a split cylindrical member having a pair of open ends that is sized to be mated within the interior of the holder assembly 40 and which engages the cylindrical side wall 60 of the support portion 56. The outer diameter of the retaining insulator 52 is sized to be placed in intimate compressive contact within the holder assembly 48 wherein the outer diameter is slightly larger than the diameter of the monitor crystal 44 and the retaining cavity 32. In addition, the retaining insulator 52 has an extending flange 68 that engages the top of the cylindrical side wall 60 of the holder assembly 48. The monitor crystal 44 is disposed between the support portion 56 of the holder assembly 48 and the bottom of the retaining insulator 52 when assembled, whether intimately or with a clearance therebetween, and in which the support portion 56 is further defined by a material aperture 67, which is slightly smaller than the sensor aperture 63 of the processing chamber by about 1-2 mm, typically, enabling the face of the monitor crystal 44 to be exposed to the sensor aperture 63 when mounted within the storage structure 20.

At least one feature can be provided such as a hole (not shown) that allows the insulating retainer 52 to be easily grasped for removal when the monitor crystal 44 needs replacement and after the package 40 has been removed from the storage structure 20. This additional feature may alternatively be the extending flange 68, which has the additional benefit of not allowing the insulating retainer 52 to drop into the retaining cavity 32 of the storage structure 20 supporting the monitor crystal 44 and contact the crystal 44 or further complicate the removal of the insulating retainer 52. To that end, the extraction feature could also alternatively include any structure that would cooperate with a tool (not shown) or fingers to allow easy extraction of the monitor crystal 44 from the holder assembly 48.

The operation of the monitor crystal 44 requires that it become a component of either an active or preferably passive oscillating electrical system as discussed in U.S. Pat. No. 5,117,192 to Hurd, previously incorporated herein. To that end, it is required that electrical contact to both the front and rear surface of the monitor crystal 44 be maintained. It is therefore necessary in the conventional means of exciting a monitor crystal 44 that the holder assembly 48 be made from an electrically conductive material so as to insure low resistance contact to the front or deposition face or that a separate means of electrical contact be provided. It is also possible to electrically excite the monitor crystal 44 in what is termed a parallel drive (not shown), which requires electrical access to only one major surface and as described in Parallel Field Excitation of Thickness Modes of Quartz Plates., R. Bechmann, 14$^{th}$ Annual Symposium on Frequency Control, (1960) and Design and Testing of a Lateral Field Excited Rate Monitor for Use in Thin Film Deposition Systems., Kristopher Sqambato, Thesis for MBA, University of Maine (2008). While parallel excitation has some advantage in execution, its performance for the purpose of deposition monitoring and control is not generally advantageous and usually leads to reduced coating life.

It should herein be noted that the sensitivity of a quartz or other piezoelectric crystal as a mass sensing/measurement tool is not dependent on its diameter. That is, the basic mass sensitivity is set by the angle of plate cut relative to the basic lattice axes and the resonant frequency of the uncoated crystal unit. Within reasonable limits, it is possible to choose a monitor crystal 44 that is sized for convenience of use or a size that is practical to handle during installation or even more importantly during the shaping operations employed during manufacturing. With proper shaping of the monitor crystal package 40, it is quite feasible to reduce the diameter of a piezoelectric crystal 44 from the diameters commonly deployed (e.g., 12-14 mm) to less than about 8 mm without dramatically changing the design concept or manufacturing tools.

As discussed infra and for purposes of deposition measurement and control, it is often important to have a large number of piezoelectric crystals 44 available to insure that rate control and accurate thickness termination can be maintained through the increasingly larger number of substrates coated over increasingly longer intervals between coating tool maintenance. In addition, it is almost never the case that there is a large unused volume in the coating tool that might be devoted to provide for large numbers of piezoelectric crystals ready for use. Therefore, a situation exists where available space is limited and a premium is attributed to any device that is able to deliver high capacity without a commensurate use of the limited space within the vacuum enclosure. It is thereby justified and advantageous to minimize any volume associated with measurement and maximize the number of possible monitor crystals 44 that can be placed into sequential service using this apparatus. Although not essential to the working of the herein described exchange device, it is valuable to have a design that utilizes space efficiently and this is aided by using a monitor crystal as small as is practical to utilize at the time of design. The reduction of monitor crystal size accrues into size reduction of the entire design, including the holder package 40 and storage structure 20. A reduction in monitor crystal size reduces the size of the holder, which reduces the size of the organized storage structure. Smaller monitor crystals can be arrayed closer together in the organized storage structure so for the same number of crystals less travel distance is required of the organized storage structure. From the use of a smaller monitor crystal, substantial savings in utilized volume accrue.

As discussed herein and referring to FIG. 2, the monitor crystal package 40 is inserted into one of many possible specially shaped retaining cavities 32 formed into the organized three-dimensional storage structure 20. It is necessary to maintain the position of the holder package 40 within the retaining cavity 32 to insure continued electrical contact and the holder package's proper physical location both with respect to its individual cavity 32 on the three-dimensional storage structure 20 and in a fixed relationship with all other similar cavities 32 of the storage structure 20. To this end, a holder retainer spring 65, shown herein as a wire shape, shown as inwardly directed toward the retaining insulator 52 with a concave engaging surface, is just one of many possible retaining devices useful for this purpose. It will be readily apparent that other means for providing retention of the holder can be provided, including springs and other suitable structures formed of resilient materials or designs that provide sufficient range of compression to engage the support portion 56 of the crystal holder 48 and physically connect it to the retaining cavity 32 of the organized storage structure 20. An insulator 73 is a two-piece insulating structure that provides both positional stability and electrical isolation for the holder retainer spring 65, as well as a contact screw 75 that is engaged from the rear 33 of the retaining cavity 32 through aligned openings in the insulator 73. A telescoping contact spring 71 is disposed between the bottom of the insulator 73 and the retained monitor crystal 44. The telescoping spring 71 is retained by a nut 74 and split lock washer 76 threadingly secured on the shank of the contact screw 75, the latter being retained to the top portion of the insulator 73 using a corresponding washer 78. When assembled, the head of the contact screw 75 protrudes radially inwardly towards the hollow interior of the storage structure 20.

Figure 3:
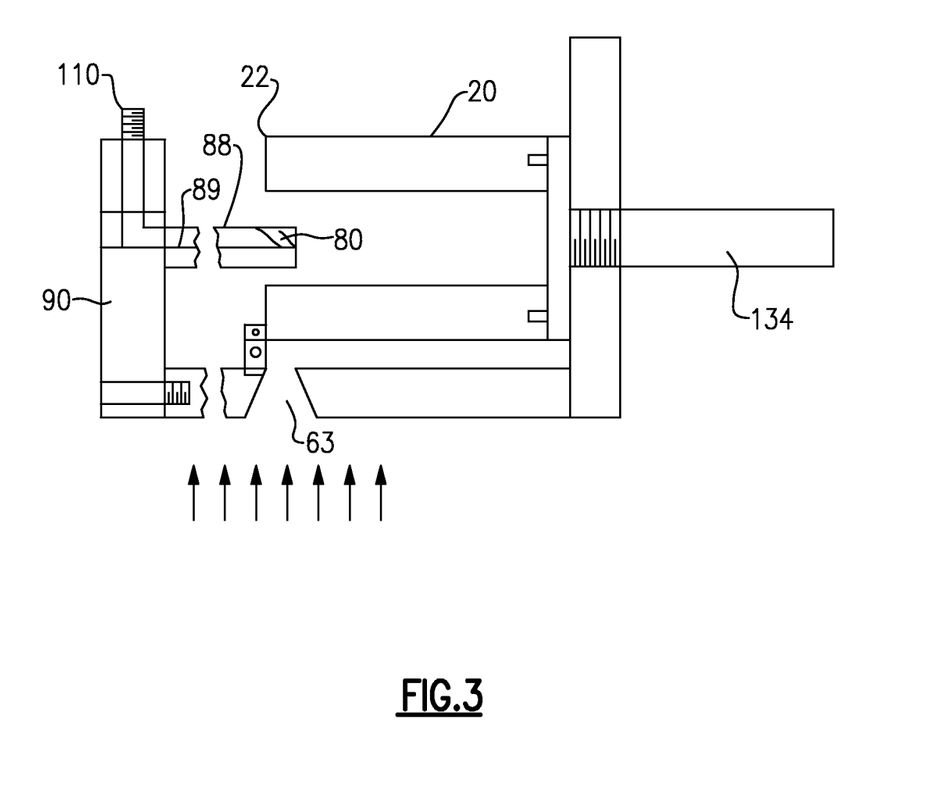
FIG. 3 is a side elevational view of the three dimensional storage structure as engaged with a brush contact assembly.
Figure 4A:
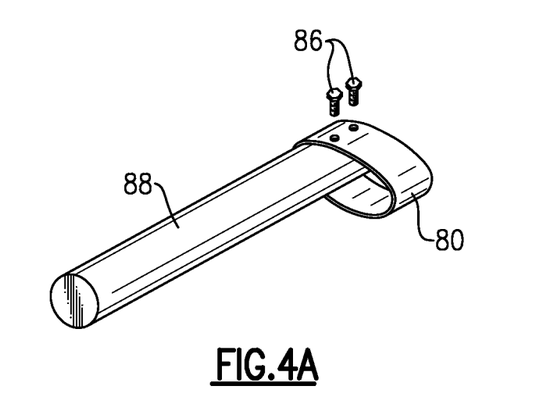
FIGS. 4A and 4B depicts portions of the brush contact assembly.
Figure 4B:
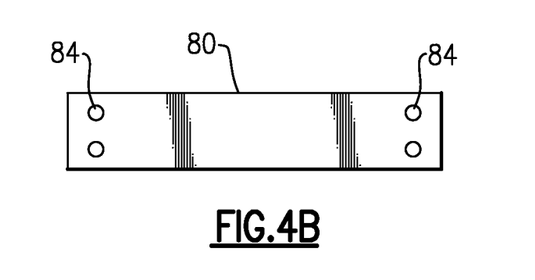

According to the exemplary embodiment, a brush contact system is herein provided for creating the necessary electrical contact to a retained monitor crystal 44. An essential feature of the brush contact system is that it should work easily and reliably in two (2) fully opposed wiping directions in relation to the advancing storage structure 20. As depicted in FIG. 4A, an exemplary brush contact 80 initially is a flat piece of metal with two or more holes 84 sized for receiving small screws 86. In this version, it is essential that the brush contact 80 be conducting and sufficiently flexible so as to be bendable, as shown in FIG. 4B. Alternatively, the brush contact could be defined by a series of conductive bristles, a formed wiping spring, or other form of moving contact. The distortion of the brush contact 80 as it wipes across the head of the contact screw 75 requires sufficient force during rotation of the storage structure 20 to provide the deformation. If the brush contact 80 is very stiff and unyielding, it requires a commensurately large force to align with the brush contact 80. If the force required is too large, the mechanism required to drive the storage structure 20 must be very powerful and the likelihood of wear and significant particle generation is increased. If the force required to distort the brush is very low, a less than ideal electrical contact might result. This force required for distortion may be controlled by the choice of thickness and width of the material chosen for the fabrication of the brush contact 80, as well as the diameter the contact takes when the brush contact is wrapped in a substantially cylindrical form around the end of an insulating contact post 88, which diameter is controlled by the separation between the pair(s) of holes 84. Referring to FIG. 3, the contact post 88 is fixedly disposed and extends longitudinally from a fixed mount plate 90 that extends toward the first end 22 of the three dimensional storage structure 20. In this embodiment, the front end of the storage structure 20 is open thereby accommodating the extending brush contact 80 and contact post 88. The brush contact is therefore fixed and caused to contact the protruding head of the contact screw 75 associated with a retaining cavity 32 that has been advanced by the drive mechanism relative to the measuring position, such as shown in FIG. 2. It is essential that the brush contact be sufficiently narrow in terms of configuration so as to contact a contact screw 75 associated with a single retaining cavity 32 of the storage structure 20, such that only one monitor crystal 44 is excited via a resonance circuit.

In some cases, it may be desirable to place a coating on at least one major face of brush contact 80 in order to reduce contact resistance, improve wear or both. This flat structure has sufficient length between the screw holes 84 so that when it is wrapped around the insulating contact post 88 such that one hole from each end of the originally flat brush contact structure is captured by a screw fastener 86, it is constrained and forms a cylinder that it somewhat larger in diameter than the insulating contact post 90 and brought into tangency at the fastening point. Although one screw fastener 86 would work in many cases the use of 2 or more provides constraint from twisting of the brush contact 80 relative to the brush contact post 88. This structure has the property of being approximately isotropic in terms of resistance to mechanical deformation when the moving contact screw 75 is allowed to wipe across the brush contact 80 from the two allowed opposing directions. A conducting wire 89, FIG. 3, ultimately leading to the deposition controller (not shown) will typically be attached to one or more of the screw fasteners 36 for the purpose of establishing electrical connection from the crystal 10. An effective electrical contact path is sequenced through the contact screw 75, the telescoping contact spring 71, one face of the monitor crystal 44, a second opposite face of the monitor crystal 44 (now ground side), the support portion 56 of the holder assembly 48, the holder retainer spring 65, the storage structure 20, including a main adjustment plate 140 thereof as well as the brush contact 80, and finally through an electrical connector 110 that is connected to an electrical source capable of exciting the crystal 44 and placing same into resonance. The conducting wire 89 is held in intimate physical and electrical contact to the brush contact 80 by the fastener 86. The use of a fixed contact screw 75 that does not transmit any of the generated contact force from the brush contact 80 to the holder package 40 helps insure that the holder package 40 is not being urged out of its intended location within the retaining cavity 32 of the storage structure 20.

In herein described preferred embodiment, the arrangement of monitor crystals 44 is structured as a cylinder populated with monitor crystal packages 40 and the associated monitor crystals 44 arrayed in a helical pattern on the outward facing exterior surface 28. As defined herein, a pitch is defined as the number of monitor crystals 40 one would encounter when advancing along the helical pattern over a 360 degree rotation of the cylinder of the storage structure 20 about its major axis. In this way, a helically organized storage structure 20 is generically defined by the number of monitor crystals 44 in a pitch and the number of pitches. Total capacity of the storage structure 20 is defined as the product of the number of pitches and the number of monitor crystals 44 in an individual pitch. The overall size of the storage structure 20 is governed not only by its capacity for monitor crystals 44, but also the size of the individual monitor crystals 44 and their associated packages. It is not, however, necessary for the monitor crystal 44 to be enclosed into a package 40. That is, monitor crystals 44 might be directly placed into an appropriate structure 20 directly, but at the cost of somewhat greater difficulty in loading and unloading monitor crystals 44 during their replacement.

Organized storage structures that are not cylindrical in nature are certainly possible, though the drive mechanisms that would be used in conjunction with these latter structures could require substantially higher complexity to account for the non-simple and non-repetitive mechanisms required for indexing all possible monitor crystals 44 supported by the storage structure to the predetermined working location (adjacent the sensor aperture 63). Exemplary storage capacities and arrangement are possible, such as:

a→6 pitches of 15 monitor crystals 44 per pitch for a capacity of 45 monitor crystals b→3 and ⅓ pitches of 15 monitor crystals 44 per pitch for a capacity of 50 monitor crystals c→2 pitches of 15 monitor crystals 44 per pitch for a capacity of 30 monitor crystals d→1 pitch of 20 monitor crystals per pitch for a capacity of 20 monitor crystals. These arrangements are exemplary and therefore a variety of others can easily be contemplated.

Referring back to FIG. 1, the drive mechanism 120 herein described has essential requirements to provide for location stability of the organized storage structure 20 and a general means of placing at least one retained monitor crystal 44 into a predetermined position in relation to the sensor aperture 63 of the processing chamber. In the exemplary embodiment, the drive mechanism 120 will methodically and sequentially advance the individual monitor crystal packages 40 held by the organized storage structure 20 into the desired relation with the sensor aperture 63 using a rotary input motion that produces both rotational, as well as corresponding axial motion. While not essential to the invention, it is often convenient to drive a mechanism of this type with a motor and it is even further convenient to advance or retreat from a measuring position to the next by a full turn or 360 degrees of rotation. According to one exemplary version, the required rotation of the organized storage structure 20 is 360 degrees plus a fraction of 360 degrees that is equivalent to the angular displacement between adjacent monitor crystal locations that are on the same pitch. For example, if the organized storage structure 20 has 15 individual monitoring positions on a single pitch, the required rotation of the organized storage structure is 16/15 of a full turn. In general, for a structure with n crystals per pitch the required rotation is (n+1)/n of a full turn. Simplifying such a required movement may be accomplished with a gear train that has an overall ratio from the drive shaft to the output shaft that is simply equivalent to the same (n+1)/n ratio. This has intrinsic value even if a complex driving scheme such a stepper motor is chosen for automatic operation. A typical 2 pole stepper motor has 200 natural positions or steps in a full 360 degree revolution, or 1.8 degrees per step. For the case of 10 monitor crystals per pitch, there is an ideal position for each monitor crystal when directly driven by the stepper motor as each position is 20 steps or 36 degrees apart. In the case of 12 crystals per pitch, some of the monitor crystals will actually not be in the ideal position by as much as almost a degree. This mis-registration can lead to small, but sometimes significant errors induced by variation of the deposition impinging on the monitor crystal from that misplacement. In general, if the angular displacement between monitor crystals along a pitch is not an integer number of 1.8 degree intervals the use of a common 2-pole stepping motor will induce the aforesaid type of error. Actually, the practice of micro stepping a 2-pole motor could essentially eliminate this problem, but this latter solution would require use of a more complex drive mechanism that is capable of varying the applied current between phases. Furthermore, the motor of this more complex drive system would likely have to remain energized to hold these positions and therefore greater power consumption and heat developed are consequences. A typical 2-pole stepper motor has sufficient holding force without applied current to maintain position at the 1.8 degree intervals described according to this exemplary embodiment and therefore operates much cooler.

One method of exchanging monitor crystals in a preferred embodiment of the design is to simultaneously turn and advance the organized storage structure 20 through a combined rotation and advancement or if the rotation is reversed, a corresponding retreat along the storage structure's primary cylindrical axis such for test purposes or replacement of at least one monitor crystal 44. This motion can be directly produced by rotating an advancing screw 134 with a thread pitch that is equal to the number of monitor crystals 44 in a pitch divided by the displacement between adjacent pitches of monitor crystals 44. In this advancement scheme in order to utilize all of the crystals 44 on a single pitch, the helically organized storage structure 20 is required to rotate one more turn than is the number of monitor crystals 44 on the pitch when all of the monitor crystals on the pitch are sequentially utilized.

In the exemplary embodiment, a rotation greater than 360 degrees is required as previously described. This rotation is chosen in preference to a fractional turn between adjacent monitor crystals 44 in order to avoid steep thread pitches that have an inherently higher friction and greater tendency to weld in a high vacuum environment, especially if elevated temperatures are present. In the described means of monitor crystal advancement the motion provided by the drive mechanism cannot be limited to simple rotation at a fixed point of drive. Because of the simultaneous linear displacement of the advancing screw 134, a means must be provided that allows for that displacement without loss or distortion of the angular position. A simple means of accomplishing this is to provide for one or more gear faces with sufficient width across the face to allow one gear to simultaneously rotate and slide along a tooth face to make up for the displacement simultaneously taking place with the forced rotation. This sliding motion, while not desired in a high speed or high load gear train, is acceptable in a slow speed low load application. The issues induced by the gears sliding against each other may be further mitigated by adding a hard or wear coating, such as nitrogen ion implantation, titanium nitride or diamond like carbon, to at least one of the gears involved in the sliding component of the motion.

The gear train chosen for this application will have features essentially as depicted in FIG. 1. The advancing screw 134 passes through a main structural plate 140 where it either mates directly with female threads formed in the plate or those of a replaceable threaded component 143 inserted into an alternate main structural plate 140', shown in FIG. 5. It can be advantageous to have the threads of the advancing screw 134 or the mating female threads coated with a wear enhancing/friction reducing coating, such as titanium nitride or a similar material. The advancing screw 134 is connected in a rigid, yet easily removable and replaceable manner to the organized storage structure 20. The other end of advancing screw 134 is attached to a traveling gear 144. The important attribute of the traveling gear 144 according to this exemplary embodiment is that it have a number of teeth that is an integer multiple of the number of monitor crystals 44 in a single pitch of the organized storage structure 20. For this gear and others used herein, a plain rather than helical gear design is preferred to minimize the contact between mating gear faces as gear contact points are exchanged during rotation. This improves the tendency of the gears to slide laterally as necessary during the rotation of the advancing screw 134. It is important to keep minimum friction in all of the rotating components, yet provide sufficient mesh between that mating gears to minimize the looseness between teeth (i.e., "backlash"). This control of mesh is through the use of high tolerance gears and maintaining proper and controlled positioning between the gear axis. In some cases it might be useful to have adjustable means of fine adjustment of relative gear positioning to further reduce the backlash or to employ anti-backlash style gears for the traveling and/or driving gear.

In order to accommodate the linear motion necessary to advance the helically organized storage structure 20, a single gear of sufficient length to accommodate this motion must be provided to drive the traveling gear 144. This will be known as the intermediate driving gear 148 in this description. The intermediate driving gear 148 may, in principle, be formed with any practical number of teeth that are designed to mesh properly with the traveling gear 144 and sufficiently long to maintain mesh and hence a proper phase relationship as is necessary for the full number of monitor crystals 44 to be accessed on the storage structure 20. As a matter of convenience, the intermediate driving gear 148 should have a number of teeth such that a single 360 degree rotation of this gear 148 will advance the traveling gear 144 and the attached organized storage structure 20 to the next monitor crystal's 44 position. The ratio of teeth of the intermediate driving gear 148 to teeth of the traveling gear 144 is optimally $(n+1)/n$ which is that portion in excess of a single turn that the traveling gear 144 is required to advance or retreat to the next monitor crystal's 44 position on the organized storage structure 20 when the number of crystals 44 evenly spaced on a single pitch of the organized storage structure 20 is n.

Power for monitor crystal advancement or retraction may be applied directly to a shaft extension 152 of the intermediate driving gear 148 or through another gear (not shown) in permanent mesh with it. In either case, one full 360 degree turn of the intermediate driving gear 148 will conveniently move the next available monitor crystal 44 into the measuring position. As stated previously, it is only a matter of convenience that crystal exchange be induced by a full rotation; fractional turns or multiple turns would be equally functional, but just less convenient. In some cases, it may be desirable to reduce the number of teeth to significantly reduce the inertia of the intermediate traveling gear 148. In this case, selecting a ratio that is an integer fraction is useful if this gear 148 were directly driven.

Alternatively, it is also reasonable to eliminate the intermediate gear and directly drive the traveling gear 148 with a driving gear having the additional property of having a gear face that is sufficiently wide to cover the lateral motion of the traveling gear while maintaining constant tooth engagement.

For example and still referring to FIG. 1, a stepper motor 156 can be mounted in a manner to engage either the extension shaft 152 of the intermediate driving gear 148 or alternately with a driving gear 160 attached to the stepper motor 156 and directly engaging the teeth of the intermediate driving gear 148. The advantage of utilizing a plain driving gear is that it allows the intimate mounting of the stepper motor 156 to the main structural plate 140 and the benefits of any temperature control applied to the structural plate 140 are inured for the removal of the motor's waste heat directly through conduction. It is well known that because in vacuum there can be no convective heat loss and radiated transfer is very inefficient when limited by the maximum functional temperatures of normal insulating materials used in the construction of stepping motors that a well-designed conductive thermal path is preferred in order to avoid insulation failure due to over temperature of the motor windings.

The driving gear 160 should have a number of teeth equivalent to the intermediate driving gear or an integer multiple, again only for convenience in keeping position advancement of the monitor crystal 44 simple. It is also possible to utilize a driving gear 160 having fewer teeth than the intermediate driving gear 148. For example, if the ratio were such that two complete revolutions of the driving gear 160 were to invoke a single and complete 360 degree rotation of the intermediate driving gear 148, a relatively easy and simple rule for incrementing or decrementing to the next monitor crystal 44 can be utilized and the benefit of reduced torque requirements for any driving mechanism might be realized. Ultimately, it is only the ratio of the driving gear 160 to the traveling gear 144 that is essential for maintaining ratio. Of course it is easy to envision a situation in which the gear ratio might be further increased so that 3 or 4 or even more complete driving gear 160 revolutions could be required to advance the intermediate driving gear 148 one revolution and the torque requirement for this advancement of position action even further reduced. It is also possible to correct for the mismatch in stepper motor rotational step intervals, which according to this exemplary embodiment are 1.8 degrees, and the need for other logical intervals through a judicial choice of driving and driven gear ratios. For example, if a total of 15 monitor crystals 44 are arrayed on a single helical pitch, the angular spacing between sequential monitor crystal positions is 24 degrees. This spacing requires either a 24 degree rotation, which is not an even multiple of 1.8 degrees (actually 13.33 steps) if a steep pitch advancing screw 42 is used or if the preferred method of requiring more than a complete turn is used (360+24=384 degrees) 213.333 steps are required for proper positioning of the next monitor crystal into the proper place relative to the sensor aperture 63. It is clear that a direct drive of the advancing screw 134 can lead to some complexities that are avoided with the correct choice of gear ratios.

Alternatively, it may become necessary or more convenient to power the storage structure 20 in some manner that requires the driving impetus to approach in a direction that is not in the general direction of the axis of the intermediate drive gear 148. The use of a crown gear (not shown) meshing directly with the intermediate driving gear 148 such that the mesh between the two gears is at two points or even at one point may be simply accommodated with the addition of a rigid bracket containing a bearing surface in an alignment conducive for the proper mesh of the crown gear and the intermediate drive gear 148. It is also easy to add a bracket that would accommodate the proper meshing between a driving bevel gear and a driven bevel gear that attaches to the intermediate driving gear shaft extension 152. Although it is normal that the rotational axis of bevel gears are assumed to be 90 degrees displaced between the driving gear and the driven axis of rotation, it is possible and easy to build bevel or miter gears designed to mesh at other angles to accommodate a large range of possible input powering situations.

In passing, it should be noted that though all prior discussion relates to a defined storage structure having at least one defined helical path for indexing monitor crystals, other path configurations and drive mechanisms are easily contemplated with regard to the three dimensional designs discussed herein. For example, a plurality of monitor crystals (e.g., 25-30) could be retained using holder assemblies as previously described according to FIG. 2 along a circular circumferential path on the exterior lateral surface 28 of the storage structure 20. In this latter configuration, the drive mechanism is somewhat simplified in that a traveling gear would not be required.

Figure 5:
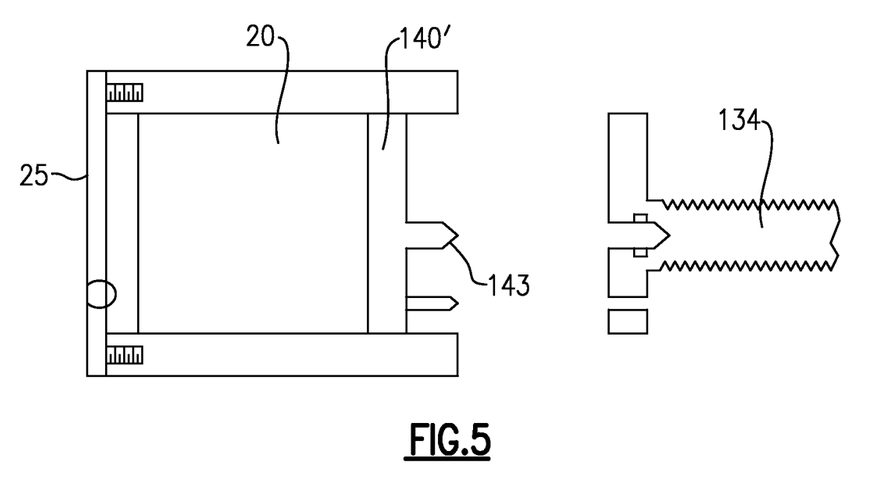
FIG. 5 is a side elevational view depicting an exemplary engagement between the drive mechanism and three dimensional storage structure.
Figure 6:
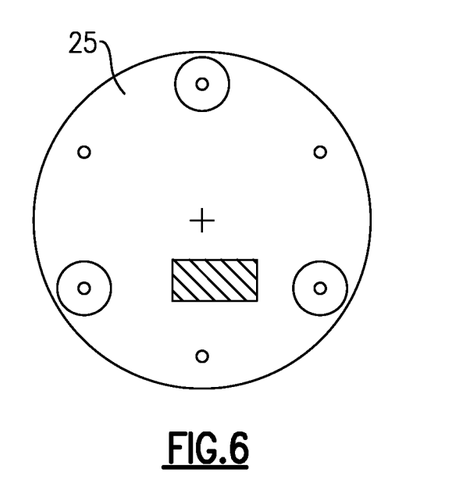
FIG. 6 depicts a front plate that can be mounted to the three dimensional storage structure, for example the storage structure shown in FIG. 5.
Figure 7:
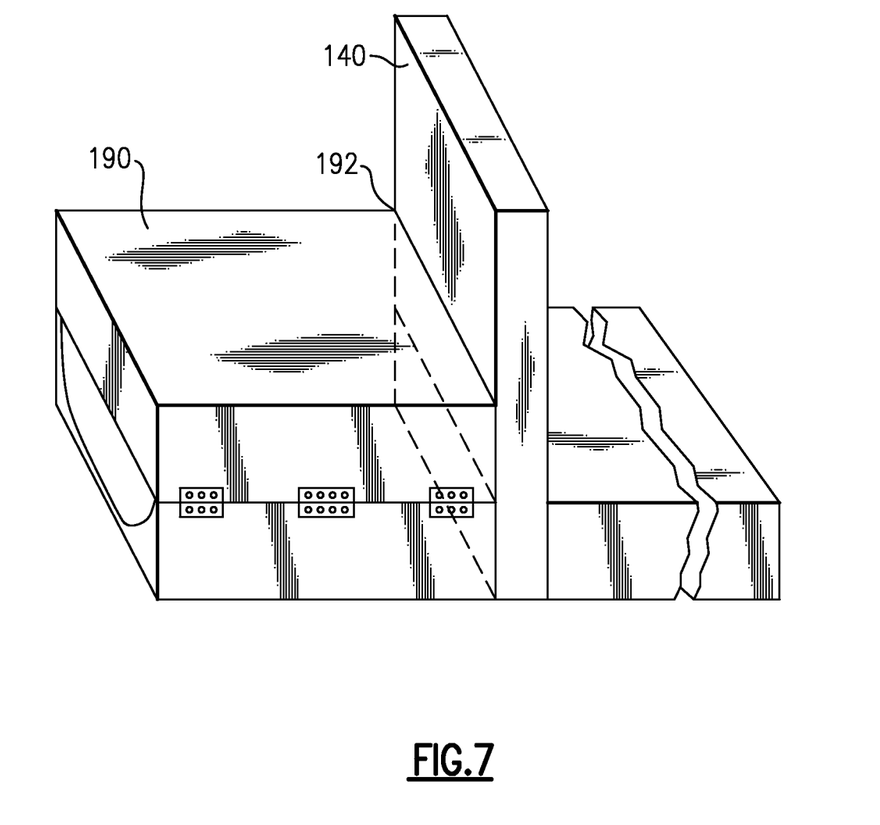
FIG. 7 is a top isometric view of a storage vault used in conjunction with the three dimensional storage structure and drive mechanism of FIG. 1.
Figure 8A:
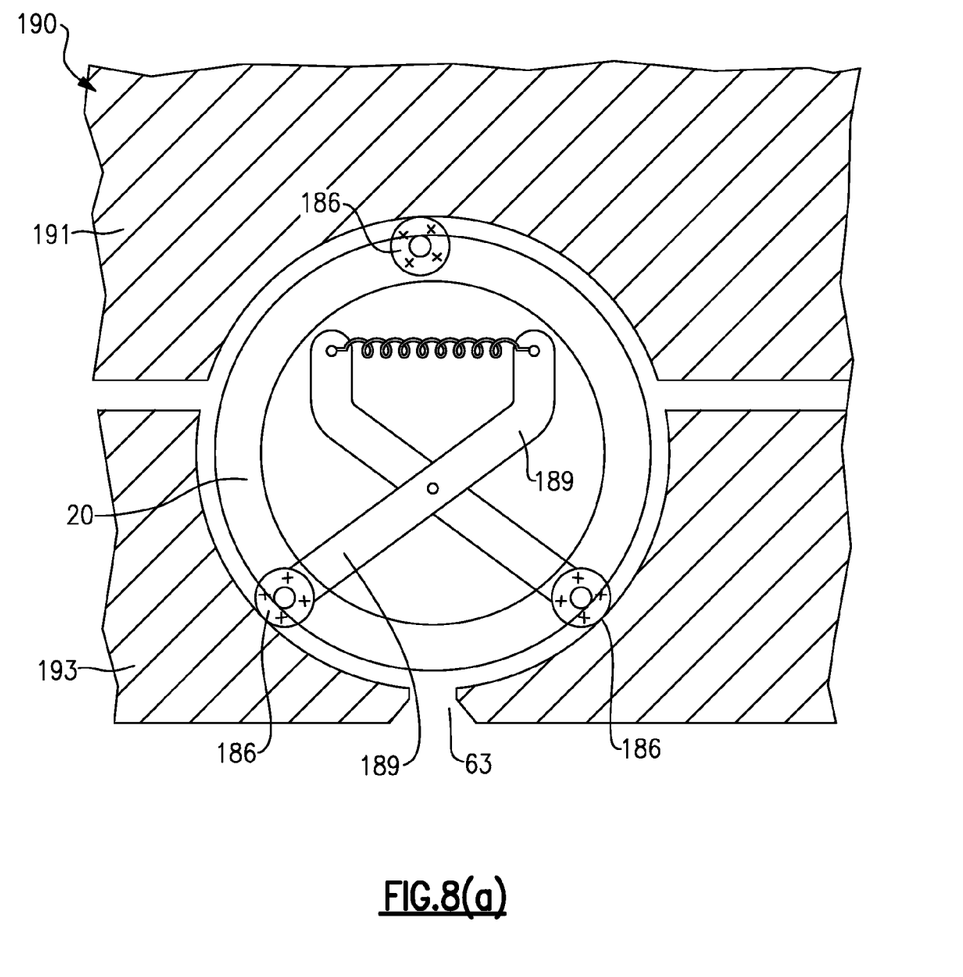
FIGS. 8(a) and 8(b) depict partial sectioned end views of the storage vault and storage structure of FIG. 7 according to exemplary embodiments that utilize ball bearing assemblies and resilient spring acting elements used for storage structure stabilization within the storage vault.
Figure 8B:
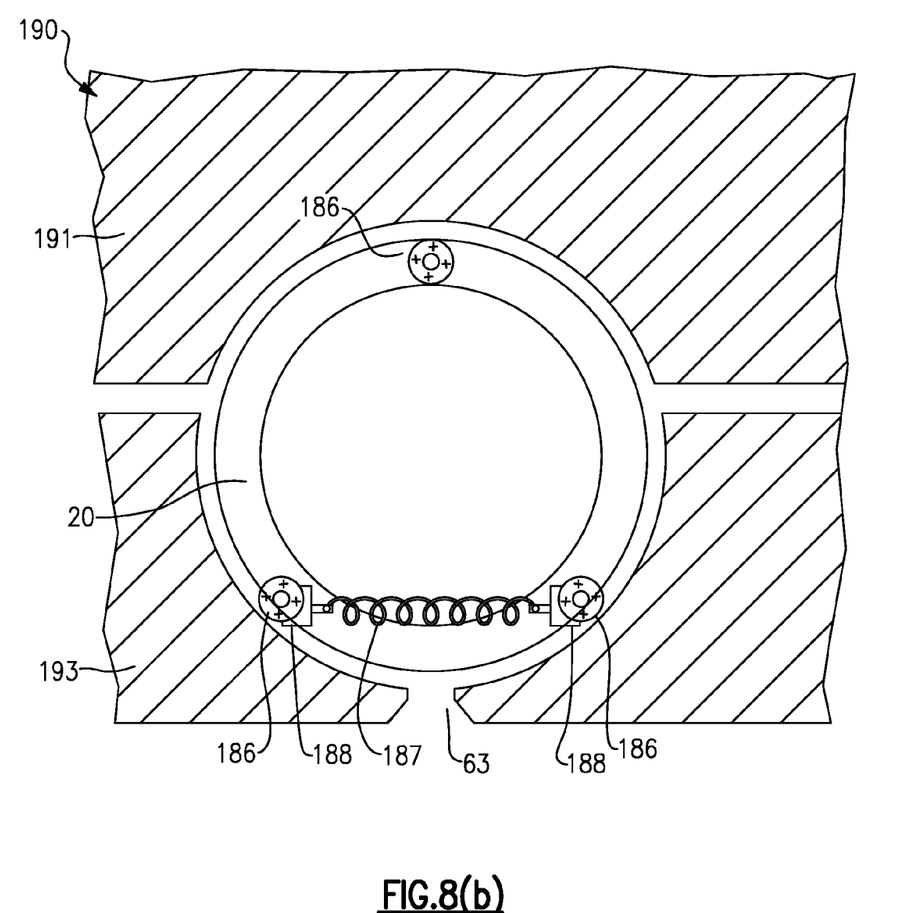

In the described embodiment, the storage structure 20 may grow in overall length in a direction that is removed from the driven end attached to the advancing screw 134. Since the storage structure 20 for a high capacity exchanger may result in many pitches, the leverage placed on the attachment to the advancing screw may be substantial. Therefore, it may be useful to provide a means of supporting the end away from the attachment and thus reduce the weight induced torque on the attachment point. According to one embodiment and as shown in FIGS. 1, 7 and 8(a) and 8(b), three or more rollers consisting of ball bearing assemblies 186 can be attached to the helically organized storage structure 20 and in which one or more spring loaded levers 189, FIG. 8(a), can be provided in order to keep the storage structure 20 centered within a storage vault 190. Alternatively and as depicted in FIG. 8(b), a spring 187 can be linked to supports 188 provided at two of the ball bearing assemblies 186. In each depicted example, an end cover plate 25 such as depicted according to FIGS. 5, 6, is not required relative to the storage structure 20. As shown, the storage vault 190 is defined by a removable upper portion 191 and a fixed lower portion 193 in which the spring loaded levers 189 or spring loaded supports 188 maintain the storage structure 20 centered between the portions 191 and 193 and also relative to the sensor aperture 63. It is helpful that the ball bearing assemblies 186 be slightly canted to the same angle as the screw pitch of the advancing screw 134, FIG. 3, to minimize rubbing and encourage rolling.

The successful operation of a crystal exchanger mechanism can be aided by the proper and judicious design of deposition material shielding. The shielding should minimally serve the following functions: i) the shielding should be easy to replace and to subsequently clean between uses; ii) the shielding should exclude material from substantially entering the storage volume and prematurely coating the monitor crystals 44 yet to be used; iii) since the shielding is the most easily cleaned and replaceable part of the structure, it alone should define the sensor aperture 63. In this way, the shielding is readily replaced and the possibility of reducing the coated diameter of monitor crystal 44 from the slow growth of material on the opening from the combined accumulation of deposition material during the use of many different monitor crystals 44 will be interrupted and corrected before the diameter is sufficiently reduced to a size no longer sufficient to cover the entire vibrating area of the monitor crystal 44. The monitor crystal 44 will not provide an accurate measurement of mass unless its entire vibrating area is coated. If the sensor aperture 63 through size reduction from accumulated deposition material reduces the coated area below this critical vibrating size, the monitor crystal 44 will thereafter provide measurements that are always less than the true mass arriving and staying on its surface. iv) the shielding must also insure a consistent spatial location for the multitude of monitor crystals being used. Without this positional location consistency with respect to both the material sources and substrates, the tooling factor, which is a geometrical ratio of the material impinging and staying on the monitor crystal 44 and that impinging and staying on the substrates of interest, will vary in ratio and thereby reduce the potential accuracy and reproducibility of the process due to variations of this controllable attribute. It is also possible by mis-registration between the active area of the crystal (defined by the material aperture 67) and the sensor aperture 63 to not fully coat the active area of the monitor crystal 44 and cause errors of the type discussed in requirement iii) above. Another problem with failure to register, especially if a portion of the vibrating area is not covered with deposition material is that the acoustic wave will have unwanted discontinuities and will cause poor resonance properties resulting in low Q and corresponding high noise and early cessation of oscillation and measurement failure.

The replacement of monitor crystals 44 or monitor crystal packages 40 is most convenient when it can be done in a clean and convenient place. It is often inconvenient to even reach the crystal exchanger in a large vacuum coating plant. The ability to easily remove the deposition shielding and perhaps a portion of the storage vault to gain access and quickly detach the organized storage structure 20 for removal from this crowded and confined area is important. As shown in FIG. 7, detachment of the described storage structure 20 from the advancing screw 134 can be aided by the use of magnets 192 or detents for ease of use, but implicit is the need for rigidity and uniqueness of position of whatever mechanism is chosen.

It is also advantageous that efficient heat transfer from the monitor crystal 44 through other structural elements so a stable temperature environment be provided for maximizing measurement precision. Using a metal holder assembly 48 is preferred over other material classes for its higher electrical and thermal conductivity. The frequency stability of a typical quartz piezoelectric crystal, even one optimized for frequency stability around room temperature, such as the AT cut of single crystal quartz, is enhanced and the measurement stabilized to a higher degree if the environmental temperature is restricted in range. To this end, minimizing temperature variation and increasing the flow of heat from or to the temperature controlled area, as discussed subsequently, has a positive effect on the operation in practice of any high capacity crystal exchanger, such as described herein.

Referring to FIG. 1, the details of an exemplary thermal exchange passage 196 is added to the main structural plate 140. This thermal exchange passage 196 is preferably continuous, hermetic and avoids intersecting any mounting holes, attaching screws or shaft passageways that are part of or attached to the main structural plate. The passage can be formed, for example, by drilling two (2) approximately parallel holes that do not reach the far side. These holes are connected by a third drilled hole that is approximately perpendicular or transverse to the first two drilled holes, intercepts and then passes through one of the first two described holes and in which the drilling stops after passing through the interception with the second described hole and terminates before completing to the far side. All of the drilled holes described are contained within the main structural plate 140 and sufficient material is present at all points to insure that there can be no passageway to the exterior surface of the main structural plate 140. It is easy to then hermetically seal the starting point of the third hole through any of the mechanical techniques of brazing, soldering or preferably placing a short plug of the same metal type as was removed in drilling and then fusing it and making it hermetic while insuring that the completed passage 196 is substantially free of debris and obstruction. In this way, a fluid cooling loop is formed integral to the main structural plate 140 that does not significantly diminish the plate's structural strength and has no additional thermal interfaces and so near optimum transfer of heat from the fluid flowing through the formed passage 196.

The process preferred in the fusing process for sealing the entry point of the third drilled hole of the cooling passage 196 would be a shielded inert gas process, such as GTAW (gas tungsten arc welding) or plasma gas welding. In the description of the cooling passage just given a fluid may be introduced through either opening and exit through the other, no importance is given to the direction of flow. The fluid provided may be water, oil or any other heat exchanger fluid that is compatible with the materials of construction. The fluid may be controlled to a small range of temperatures or allowed to vary over several Celsius degrees as would be normally encountered in a common cooling fluid source that would be found in a factory. Again, the degree of temperature stability provided the monitor crystal 44 will be related to the variation of the cooling fluid's input temperature range. The described cooling loop is preferred as it has sufficient heat exchange area and the inlet and outlet are conveniently oriented in the same direction for ease of connection to a fluid source and return. Alternatively, the cooling passage 196 can be a single pass with the inlet and outlet disposed on different sides of the main structural plate 140. According to another alternative version, an external or internal mechanical connection between a cooling loop and the main structural plate 140 can be provided.

Figure 9:
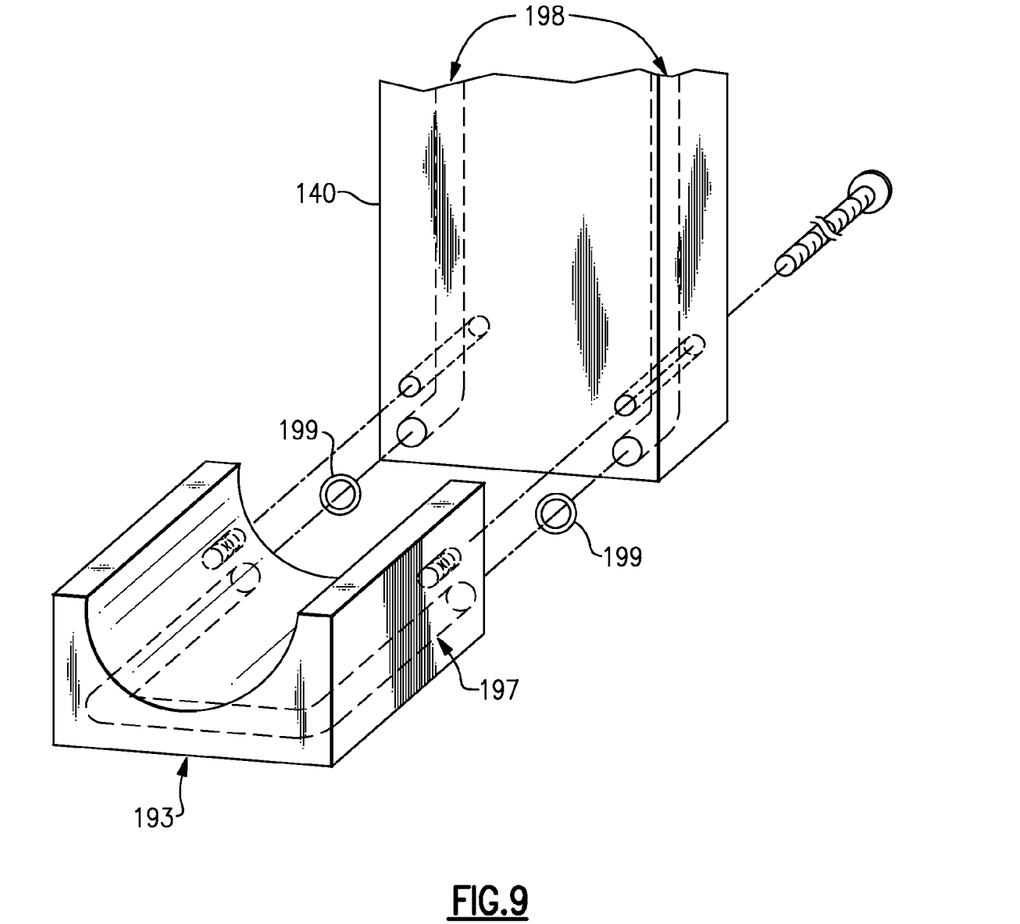
FIG. 9 is a front perspective view, partly in section and partially exploded, of an exemplary temperature controlling mechanism for the storage structure.

With reference to FIG. 9 and alternatively or in combination with the foregoing, the water cooling can also extend so as to include the fixed portion 193 of the storage vault 190. This water cooling extension would be developed using many of the above described features, but would require not drilling the third transverse passage, as previously discussed. In lieu of this passage, two intersecting passages 198 can be drilled in the main structural plate 140 to intercept a "U" shaped passage 197 that is formed by means previously described and extending into the fixed portion 193 of the storage vault 190. This latter intersection between the passages 198 in the structural plate 140 and the U-shaped passage 197 in the fixed portion 193 of the storage vault 192 can be sealed using O-rings 199 or similar sealing members in a conventional manner.

In addition to providing cooling to the main structural plate 140 and the stepper motor, there is much to be gained by intimately attaching at least a portion of the storage vault 190 to the structural plate 140. This will quickly remove the heat of condensation and source radiation before it can impinge on and accumulate in the organized storage structure 20 which, because it is moveable, is therefore not easy to provide strong thermal conduction for temperature control. Likewise, similar benefits are accrued from attaching the motion apparatus's structural framework to the cooling as provided by the main structural plate 140.

It is also alternatively possible to further control the temperature of the exchanger apparatus by active temperature control using for example, a resistor and RTD in a circuit that adds heat as required to maintain the exchanger's temperature slightly above the highest encountered temperature of the cooling fluid. It is also possible to provide a Peltier heat exchanger or similar apparatus in order to control the exchanger's temperature to a temperature anywhere between the highest and lowest cooling water temperature supplied or to a temperature lower or higher but within the capacity of said Peltier heat exchanger's capacity to move heat.

Parts List for FIGS. 1-9
20 three-dimensional (organized) storage structure
22 first end
24 second end
25 front end plate, storage structure (optional)
28 exterior lateral surface
32 retaining cavities
33 opening, rear
40 monitor crystal package
44 monitor crystal
48 holder assembly
52 insulating retainer
56 support portion, holder assembly
60 side wall, holder assembly
63 sensor aperture
65 holder retainer spring
67 material aperture
68 extending flange
71 contact spring
73 insulator (2-piece)
74 nut
75 contact screw
76 lock washer, split
78 washer
80 brush contact
84 holes—brush contact
86 screw fastener
88 brush contact post
89 conducting wire
90 plate
110 electrical connector
120 drive mechanism
134 advancing screw
140 main structural plate
142 replaceable threaded component
144 traveling gear
148 intermediate driving gear
152 intermediate driving gear shaft extender
156 stepper motor
160 driving gear
186 ball bearing assemblies
187 spring
188 supports
189 spring-loaded levers
190 storage vault
191 removable portion (storage vault)
192 magnets
193 fixed portion, storage vault
196 thermal exchange or cooling passage
197 U-shaped passage
198 intersecting passages
199 O-rings It will be readily apparent that other modification and variations are possible within the inventive aspects discussed herein and in accordance with the following claims. For example, at least one retained crystal that is presented/indexed relative to the sensor aperture can be used for measuring other system parameters, such as temperature using a crystal, having the property of large and near linear frequency change related to the temperature change encountered. To that end, crystals, such as AC cut crystals, can be used in order to perform this function.

The invention claimed is:

1. An apparatus for use in a crystal deposition monitor or crystal microbalance, said apparatus comprising:
   a storage structure having a primary axis extending between respective first and second ends and an exterior lateral surface between said first and second ends extending about said primary axis;

a plurality of monitor crystals supported by said storage structure at spaced positions along said exterior lateral surface;

a drive mechanism for rotating and axially advancing or retreating said storage structure relative to the primary axis such that at least one monitor crystal is advanced or retreated relative to at least one measuring position; and a mechanism for electrically exciting a crystal that has been advanced into said at least one measuring position.

2. An apparatus as recited in claim 1, wherein said storage structure comprises a plurality of cavities sized for retaining said plurality of monitor crystals at said spaced positions on said exterior lateral surface.

3. An apparatus as recited in claim 2, further including a plurality of holder assemblies, each said holder assembly being configured for supporting a monitor crystal and sized to be fitted into a corresponding cavity of said storage structure.

4. An apparatus as recited in claim 2, wherein said plurality of cavities are disposed along at least one helical path along said exterior lateral surface.

5. An apparatus as recited in claim 1, including at least one mechanism for moderating the temperature of said storage structure.

6. An apparatus as recited in claim 1, wherein said storage structure is cylindrical in configuration.

7. An apparatus as recited in claim 1, wherein said storage structure is polygonal in configuration.

8. An apparatus as recited in claim 3, wherein said mechanism for electrically exciting said crystal includes a brush contact for engaging a crystal disposed in said storage structure in relation to said at least one measuring position.

9. An apparatus as recited in claim 8, wherein said holder assembly comprises at least one means for stabilizing the position of said monitor crystals in said storage structure.

10. An apparatus as recited in claim 3, wherein said holder assemblies are selectively removable from said storage structure to allow replacement of at least one monitor crystal.

11. An apparatus as recited in claim 10, wherein said holder assemblies include at least one feature for enabling release of said holder assembly from a cavity of said storage structure.

12. An apparatus as recited in claim 8, wherein said electrically contacting mechanism comprises a brush contact assembly.

13. An apparatus as recited in claim 1, wherein said monitor crystals are piezoelectric crystals.

14. An apparatus as recited in claim 13, wherein said piezoelectric crystals are at least one of the group consisting of quartz, langasite, gallium(ortho) phosphate and barium titanate.

15. An apparatus as recited in claim 1, including at least crystal disposed in said storage structure that is configured for monitoring temperature upon excitation.

16. A three-dimensional storage structure for crystals used for monitoring the thickness of a material deposited onto a substrate in a processing chamber, said three-dimensional storage structure comprising:

a carrier body having a primary axis extending between a first end and a second opposite end, said carrier body further having a lateral exterior surface defined between said first and second ends and extending about said primary axis; and a plurality of retaining cavities disposed at spaced axial positions along said lateral exterior surface of said carrier body, each retaining cavity being sized for retaining a monitor crystal.

17. A storage structure as recited in claim 16, wherein said retaining cavities are disposed in a helical configuration along said lateral exterior surface.

18. A storage structure as recited in claim 16, including a plurality of holder assemblies, each of said holder assemblies being sized to retain a monitor crystal and further sized for fitting into a retaining cavity of said carrier body.

19. A storage structure as recited in claim 16, wherein said carrier body is cylindrical.

20. A storage structure as recited in claim 18, wherein said holder assemblies are releasably attached to said carrier body.

21. A storage structure as recited in claim 20, wherein said holder assemblies further comprise at least one feature to permit release of said holder assembly from said retaining cavity.

22. A storage structure as recited in claim 16, including a mechanism for moderating the temperature of said structure.

23. A storage structure as recited in claim 22, wherein said temperature moderating mechanism is fluid-based and is defined by at least one fluid passage to allow for the flow of fluid for one of cooling, heating and stabilizing temperature of said structure.

24. A storage structure as recited in claim 16, wherein said monitor crystals are piezoelectric crystals.

25. A storage structure as recited in claim 16, wherein at least one crystal supported by said storage structure is configured for measuring temperature when electrically excited.

26. A method of exchanging crystals used for monitoring material deposition in a processing chamber, said method comprising the steps of:

disposing a plurality of monitor crystals in spaced relation onto the exterior surface of a three-dimensional storage structure;

advancing at least one monitor crystal relative to at least at least one measuring position;

electrically exciting said at least one monitor crystal;

detecting the change of mass of material applied to a substrate in said processing chamber;

axially and rotatably advancing the supporting structure along a primary axis of the three-dimensional storage structure in order to index at least one other monitor crystal into said at least one measuring position.

27. A method as recited in claim 26, including the step of moderating the temperature of support structure during said monitoring step.

28. A method as recited in claim 26, wherein said disposing step includes the steps of retaining each monitor crystal in a holder assembly and placing each holder assembly into a retaining cavity of said three-dimensional supporting structure.

29. A method as recited in claim 28, including the additional step of removing a holder assembly following said monitoring step for replacement of said monitor crystal.

30. A method as recited in claim 26, wherein said advancing step includes the step of helically advancing said storage structure about the primary axis of said structure.

31. A method as recited in claim 26, including the steps of advancing or retreating the supporting structure along said primary axis for test purposes.

32. A method as recited in claim 26, further comprising the step of providing at least one monitor crystal retained on said storage structure for monitoring temperature.

33. A method as recited in claim 26, wherein said monitor crystals are disposed in retaining cavities defined in said storage structure.

34. A method as recited in claim 33, wherein said retaining cavities are disposed along at least one helical path.

35. A method as recited in claim 33, wherein said retaining cavities are disposed along at least one circular path.

36. A method as recited in claim 26, wherein said electrically exciting step includes the step of advancing said storage structure relative to a brush contact.

37. An apparatus as recited in claim 8, wherein each said retaining cavity includes a contact member disposed in conductive contact with a retained monitor crystal in which said brush contact is caused to engage said contact member when said crystal is advanced to said at least one measuring position.

38. An apparatus as recited in claim 8, wherein said brush contact includes a bendable section of conductive material attached to an extending end of a contact post.

39. An apparatus as recited in claim 1, wherein said plurality of crystals are disposed along at least one circumferential path along said exterior lateral surface.

* * * * *